(12) United States Patent
Lakhman

(10) Patent No.: US 7,562,938 B2
(45) Date of Patent: *Jul. 21, 2009

(54) DEVICE FOR SUPPORTING A PERSON IN A SITTING POSITION

(76) Inventor: Mikhail Lakhman, 105 Oceana Dr. East, Apt. 2B, Brooklyn, NY (US) 11235

( * ) Notice: Subject to any disclaimer, the term of this patent is extended or adjusted under 35 U.S.C. 154(b) by 0 days.

This patent is subject to a terminal disclaimer.

(21) Appl. No.: 12/080,769

(22) Filed: Apr. 7, 2008

(65) Prior Publication Data

US 2009/0050160 A1    Feb. 26, 2009

(51) Int. Cl.
*A47C 7/54*    (2006.01)
*A47C 7/42*    (2006.01)

(52) U.S. Cl. .............. 297/487; 297/485; 297/230.1; 297/230.12; 297/230.13; 297/230.14; 297/411.23; 297/411.24; 297/411.36

(58) Field of Classification Search .............. 297/487, 297/485, 4, 411.23, 411.24, 411.36, 230.1, 297/230.12, 230.13, 230.14
See application file for complete search history.

(56) References Cited

U.S. PATENT DOCUMENTS

| 2,667,913 | A | * | 2/1954 | Dustin | 297/411.1 |
| 2,769,483 | A | * | 11/1956 | Peterson | 297/411.36 X |
| 2,773,542 | A | * | 12/1956 | Chasin | 297/411.36 |
| 4,763,952 | A | * | 8/1988 | Gaudreau, Jr. | 297/411.36 X |
| 7,156,465 | B2 | * | 1/2007 | Stewart et al. | 297/411.36 |
| 7,237,844 | B2 | * | 7/2007 | Stewart et al. | 297/411.36 |
| 7,416,257 | B1 | * | 8/2008 | Lakhman | 297/487 |

* cited by examiner

*Primary Examiner*—Rodney B White
(74) *Attorney, Agent, or Firm*—I. Zborovsky

(57) ABSTRACT

A device for supporting a person in a sitting position has a substantially horizontally extending supporting element placeable on a supporting surface substantially at a level of a person's pelvis when the person is in a sitting position, and two substantially vertically extending elements each having a lower end connected with the horizontally extending supporting element and an upper end extendable to an area of person's armpits so that the upper ends of the substantially vertically extending elements are placeable under the person's armpits.

5 Claims, 4 Drawing Sheets

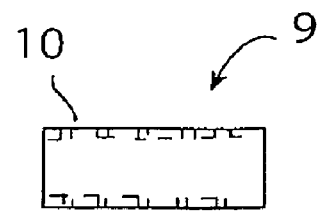
Fig. 5
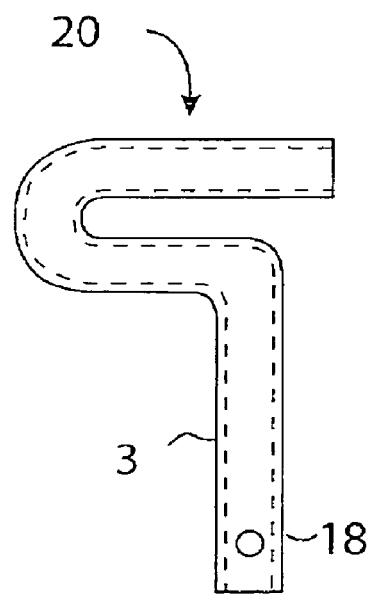
Fig. 6
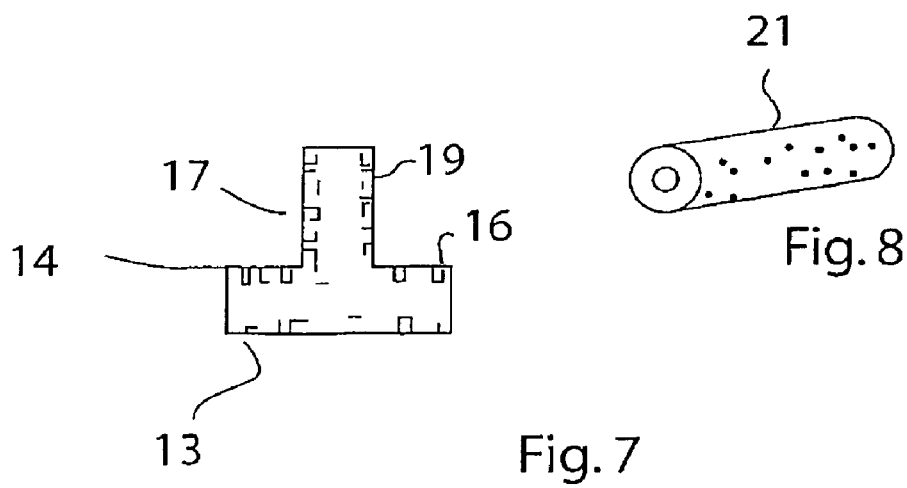
Fig. 7
Fig. 8

DEVICE FOR SUPPORTING A PERSON IN A SITTING POSITION

BACKGROUND OF THE INVENTION

The present invention relates to devices for supporting a persons in corresponding position, and in particular supporting a person in a sitting position.

It is known that some people have problems while sitting, which can be caused by some diseases of a spine, for example herniated disks, damaged spines, etc. It is therefore difficult for them to maintain themselves in a sitting position for a certain time, for example in vehicles, on benches, etc.

SUMMARY OF THE INVENTION

It is therefore an object of the present invention to provide a device which supports a person in a sitting position.

In keeping with these objects and with others which will become apparent hereinafter, one feature of the present invention resides, briefly stated, in a device for supporting a person in a sitting position, comprising a substantially horizontally extending supporting element placeable on a supporting surface substantially at a level of a person's pelvis when the person is in a sitting position, and two substantially vertically extending elements each having a lower end connected with said substantially horizontally extending supporting element and an upper end extendable into an area of person's armpits so that said upper ends of said substantially vertically extending elements are placeable under the person's armpits.

When the device is designed in accordance with the present invention it is displaced with its substantially horizontal extending supporting element on the supporting surface, for example on the seat in a car seat, on a supporting plate of a bench or a chair, etc., and the vertically extending elements extend up to the area of the armpits and support the person's torso in a vertical position so that his spine can not curve and his upper torso can not slack down.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 5 is a view showing a connecting element for connection of two parts of the substantially horizontally extending supporting element formed as a sleeve;

FIG. 6 is a view showing one of the substantially horizontally extending elements;

FIG. 7 is a view showing a T-shaped connecting member for connection of one of the substantially horizontal extending elements with the one of the substantially vertically extending elements; and FIG. 8 is a view showing a foam covering to be applied on a substantially horizontal part to be located under an armpit of the vertically extending element.

DESCRIPTION OF THE PREFERRED EMBODIMENTS

Figure 1:
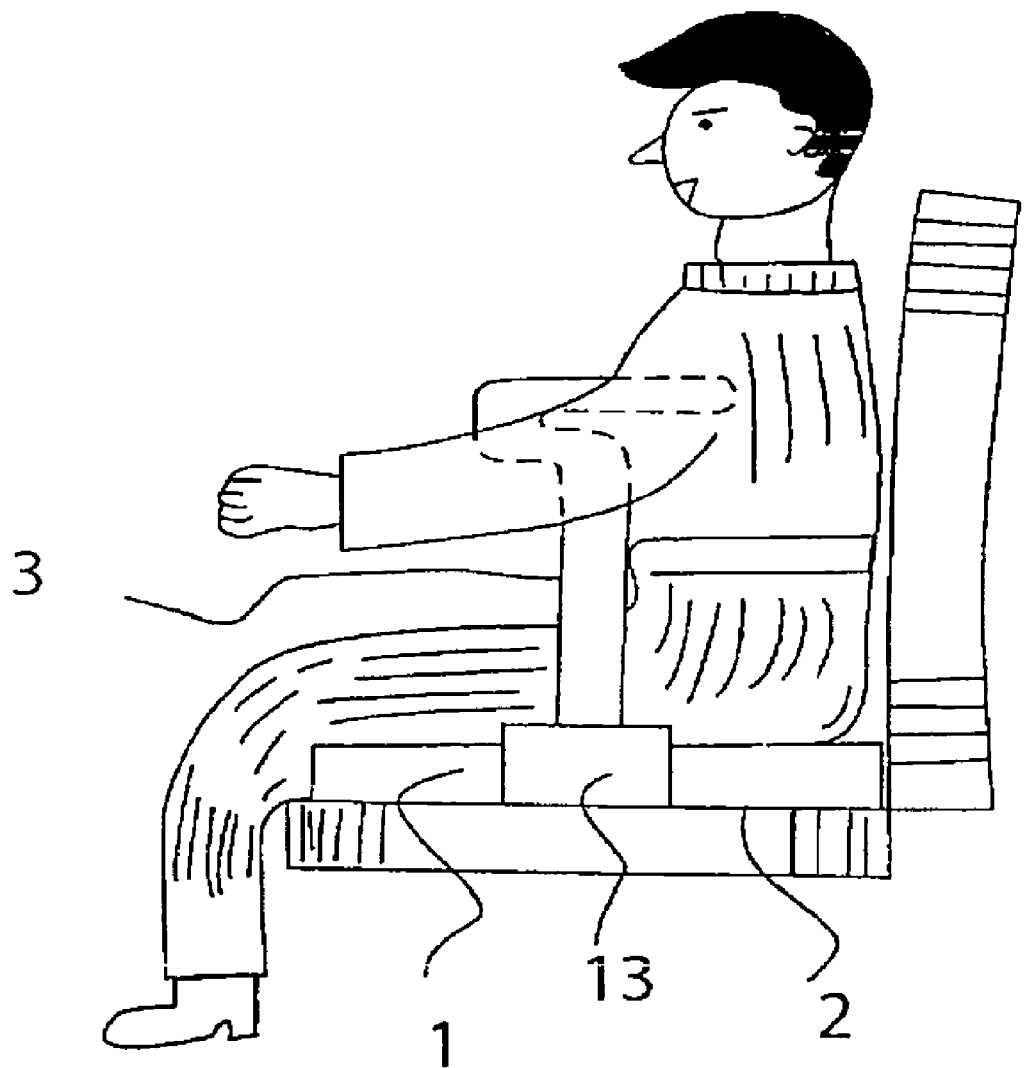
FIG. 1 is a side view of a device for supporting a person in a sitting position, wherein a person sits on a chair.
Figures 2A, 2B:
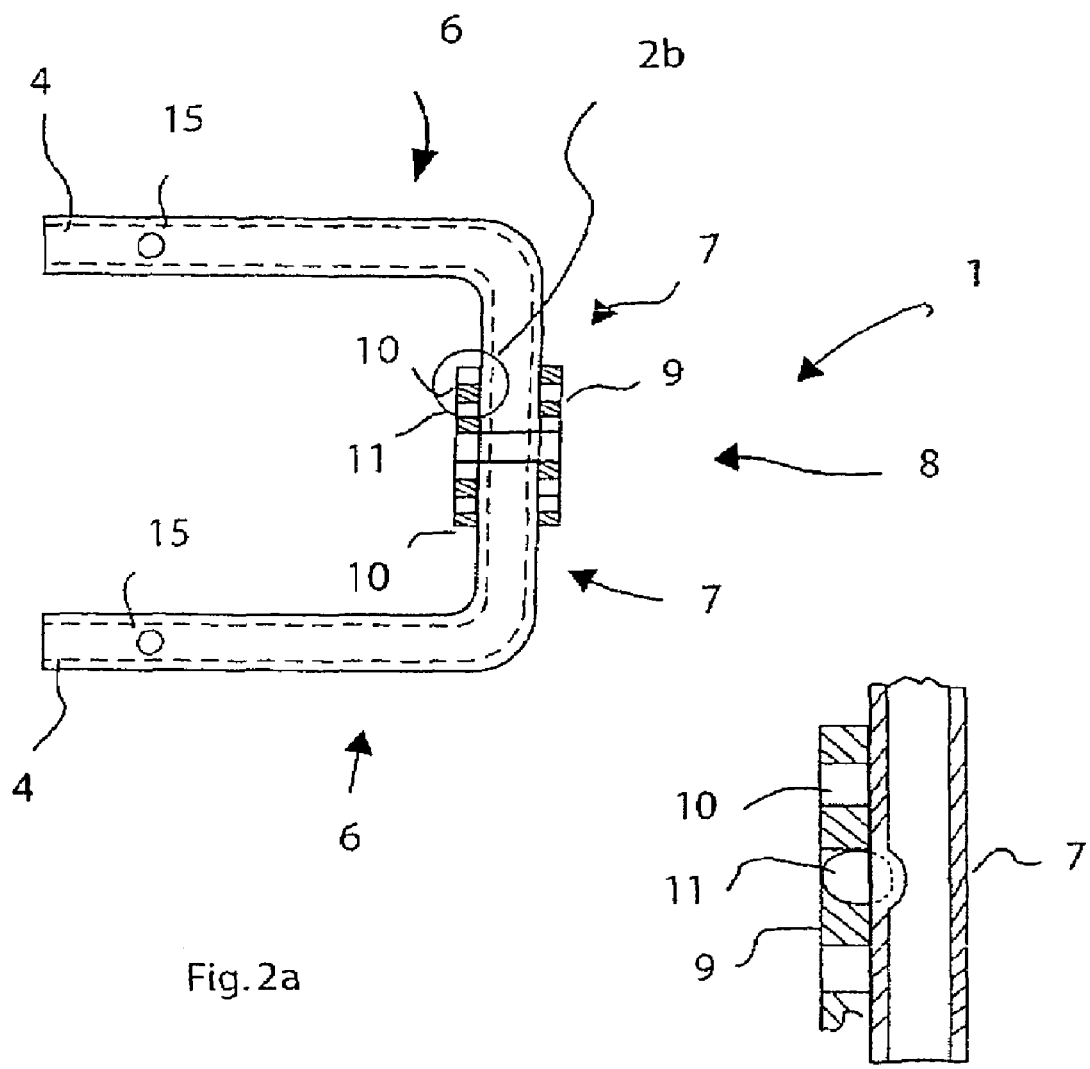
FIG. 2 is a plan view of the inventive device for supporting a person in a sitting position.
Figure 3:
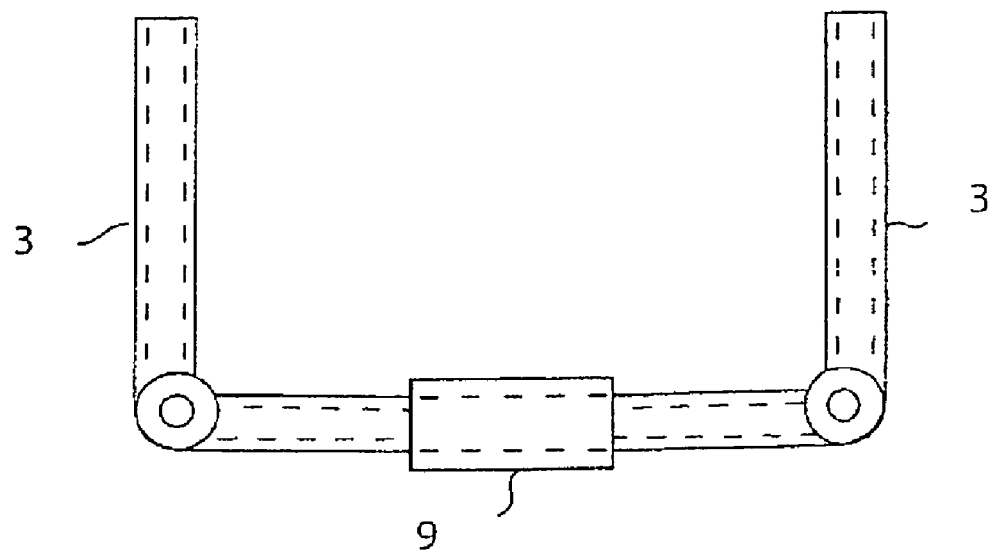
FIG. 3 is a front elevation view of the device for supporting a person in a sitting position.
Figure 4:
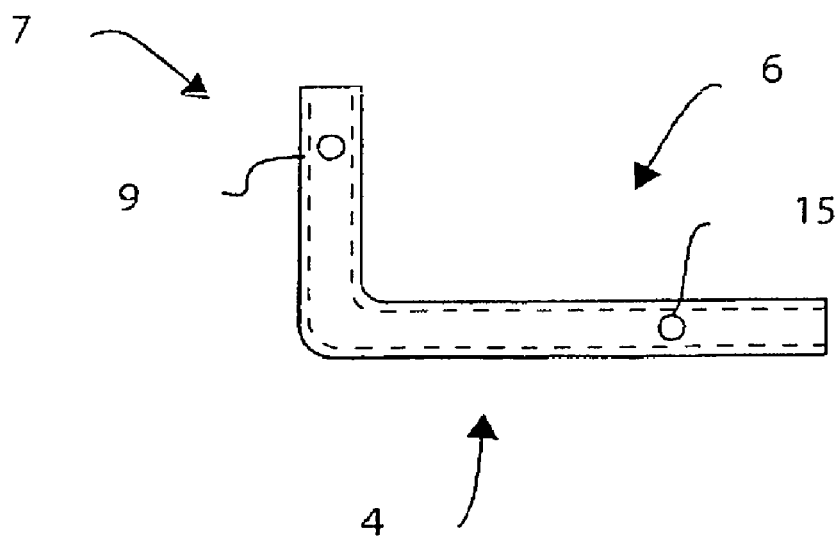
FIG. 4 is a view showing a part of the substantially horizontal extending supporting element.

A device for supporting a person in a substantially horizontal position includes a special vertically extending element 1 which is placeable on a supporting surface 2 for example on an upper surface of a chair, a car seat, etc., and two vertically extending elements which are identified with reference numeral 3.

The horizontally extending element 1 can be composed of two parts identified with reference numerals 4. Each of the parts 4 has a forwardly extending portion 6 and transversely extending portion 7. Two transversely extending portions 7 together form a transverse portion of the horizontally extending element 1. The transverse portions 7 of the parts 4 are adjustably connectable with one another, so that a transverse length of the transverse portion 8 of the element 1 can be adjustable depending on the width of a person's pelvis.

For providing such adjustment, the portions 7 can be connected by a sleeve 9 having a plurality of openings 10, while each of the portions 7 has a spring-biased stopper 11. The parts 4 can be move closer toward one another, or farther from one another and the stoppers 11 can engage in corresponding openings 10 to fix the adjusted position.

As mentioned, the supporting device has two substantially vertically extending elements 3 each connectable with the portion 6 of the part 4 in a vertically adjustable manner. For this purpose a T-shaped connecting member 13 can be used. The T-shaped member 13 has a hollow portion 14 through which the portion 6 of each part 4 extends and can be fixed in a corresponding position for example by a spring-biased stopper 15 extending in a corresponding opening 16. The lower end of the vertical element 3 is insertable into a vertical part 17 of the T-shaped member 13 and can be fixed in a corresponding vertically adjusted position, for example by cooperation of a spring-biased stopper 18 provided in the lower end of the vertical element 3 and the corresponding opening 19 of the portion 17.

By the cooperation of the elements 15 and 16 the horizontal position of the element 3 can be adjusted. By cooperation of the elements 18 and 19, the vertical position of the element 3 can be adjusted.

In accordance with the further feature of the present invention, the upper portion of each element 3 is provided with a substantially horizontal part 20. An armpit of a person in a sitting position can be conveniently placed on the horizontal part 20. For comfort, the horizontal part 20 can be covered with a coating formed for example as a foam tubular element 21.

It is believed to be clear that the elements 1, 3, 4, 9, 13, 21 are formed here, as an example, as tubular hollow elements. However, it is to be understood that they can be different. Also, it is to be understood that the corresponding connections 16, 18; 15, 19; 10, 11 can be formed in a different way rather than a stopper and an opening, to provide adjustments of corresponding parts in corresponding directions. Also, while these connections are stepped connections, there can be a stepless connection between the corresponding parts.

It will be understood that each of the elements described above, or two or more together, may also find a useful application in other types of constructions differing from the type described above.

While the invention has been illustrated and described as embodied in a device for supporting a person in a sitting position, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A device for supporting a person in a sitting position, comprising a substantially horizontally extending supporting element placeable on a supporting surface substantially at a level of a person's pelvis when the person is in a sitting position; two substantially vertically extending elements each having a lower end connected with said substantially horizontally extending supporting element and an upper end extendable to an area of person's armpits so that said upper ends of said substantially vertically extending elements are placeable under the person's armpits, said substantially horizontally extending supporting element being adjustable in a transverse direction, while said substantially vertically extending elements are adjustable in a horizontal forward direction and in a vertical direction, so that the device is adjustable in three directions in accordance with user's dimensions.

2. A device as defined in claim 1, and further comprising means for adjusting said substantially horizontally extending supporting element in said transverse direction; means for adjusting said substantially vertical extending elements in said substantially horizontal forward direction; and means for adjusting said substantially vertically extending elements in said vertical direction.

3. A device as defined in claim 1, wherein each of said substantially vertically extending elements has a lower end adjustably connectable with said substantially horizontally extending supporting element and an upper end provided with an upper horizontal part which extends in a horizontal direction over a horizontal distance to support a corresponding one of the armpits.

4. A device as defined in claim 1, wherein means for adjustably connecting each of said substantially vertically extending elements with said substantially horizontally elements extending including a hollow T-shaped element through which a side portion of said substantially horizontally extending supporting element extends and into which a lower portion of said substantially vertically extending element extends to provide a substantially perpendicularly extending orientation of said substantially vertically extending element relative to said substantially horizontally extending supporting element.

5. A device as defined in claim 1, wherein said substantially horizontally extending supporting element is composed of two parts which are connectable with and disconnectable from one another, while said substantially vertically extending elements are also connectable with said substantially horizontally supporting element and disconnectable from the latter for easy assemblying and disassemblying of the device.

* * * * *